(12) United States Patent
Kuhn et al.

(10) Patent No.: US 10,183,176 B2
(45) Date of Patent: Jan. 22, 2019

(54) THERAPEUTIC APPARATUS

(75) Inventors: Michael Harald Kuhn, Hamburg (DE); Johannes Adrianus Overweg, Uelzen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1108 days.

(21) Appl. No.: 13/131,390

(22) PCT Filed: Dec. 4, 2009

(86) PCT No.: PCT/IB2009/055509
§ 371 (c)(1),
(2), (4) Date: May 26, 2011

(87) PCT Pub. No.: WO2010/067287
PCT Pub. Date: Jun. 17, 2010

(65) Prior Publication Data
US 2011/0237859 A1 Sep. 29, 2011

(30) Foreign Application Priority Data

Dec. 12, 2008 (EP) .................................... 08171545

(51) Int. Cl.
*A61N 5/00* (2006.01)
*A61B 5/055* (2006.01)
(Continued)

(52) U.S. Cl.
CPC ............ *A61N 5/1031* (2013.01); *A61B 5/055* (2013.01); *A61N 5/1037* (2013.01); *A61N 5/1042* (2013.01);
(Continued)

(58) Field of Classification Search
USPC ........................................................ 600/411
See application file for complete search history.

(56) References Cited

U.S. PATENT DOCUMENTS 6,591,127 B1 7/2003 McKinnon
6,725,078 B2 4/2004 Bucholz et al.
(Continued)

FOREIGN PATENT DOCUMENTS

EP 1121957 A2 8/2001
EP 1974770 A1 10/2008
(Continued)

OTHER PUBLICATIONS

Greco et al: "Current Status of Radiotherapy With Proton NAD Light Ion Beams"; Cancer, Apr. 2007, vol. 109, Issue 7, pp. 1227-1248.
(Continued)

*Primary Examiner* — Patricia Park

(57) ABSTRACT

A therapeutic apparatus comprising: a magnetic resonance imaging system adapted for acquiring a set of magnetic resonance imaging data in an imaging zone, the magnetic resonance imaging system comprising a means for generating a magnetic field, —a guiding means adapted for guiding a beam of charged particles to a target zone within a subject, wherein the imaging zone comprises the target zone, a zone determination means adapted for determining the location of the target zone within the subject using the set of magnetic resonance imaging data, a trajectory calculation means adapted for calculating a trajectory of the beam using magnetic field data being descriptive of the magnetic field such that the calculated trajectory reaches the target zone, a control means adapted for controlling the guiding means using the calculated trajectory such that the beam follows the calculated trajectory.

20 Claims, 5 Drawing Sheets

(51) Int. Cl.
    *A61B 5/05*    (2006.01)
    *A61N 5/10*    (2006.01)
(52) U.S. Cl.
    CPC ............ *A61N 2005/1055* (2013.01); *A61N 2005/1087* (2013.01)

(56) References Cited

U.S. PATENT DOCUMENTS

| | | | |
|---|---|---|---|
| 2003/0125622 A1* | 7/2003 | Schweikard et al. | 600/437 |
| 2003/0130575 A1* | 7/2003 | Desai | 600/417 |
| 2005/0197564 A1* | 9/2005 | Dempsey | 600/411 |
| 2006/0245543 A1* | 11/2006 | Earnst et al. | 378/65 |
| 2007/0145281 A1* | 6/2007 | Ben-Haim et al. | 250/370.09 |
| 2007/0225603 A1* | 9/2007 | Jackson | A61N 5/10 600/436 |
| 2008/0208036 A1* | 8/2008 | Amies et al. | 600/411 |
| 2009/0088625 A1* | 4/2009 | Oosting et al. | 600/411 |
| 2009/0296885 A1* | 12/2009 | Boeh et al. | 378/65 |
| 2011/0148414 A1* | 6/2011 | Teughels | B82Y 15/00 324/316 |

FOREIGN PATENT DOCUMENTS

| | | |
|---|---|---|
| GB | 2422674 A | 8/2006 |
| WO | 9932189 A1 | 7/1999 |
| WO | 03008986 A2 | 1/2003 |
| WO | 2006130659 A2 | 12/2006 |

OTHER PUBLICATIONS

Raaymakers et al: "Feasibility of MRI Guided Proton Therapy:Magnetic Field Dose Effects"; Phy. Med. Biol. 2008, vol. 53, pp. 5615-5622.
Schulte: "The Use of High-Energy Protons in Cancer Therapy"; Loma Linda University Medical Center, Power Point Presentation, 48 pages, 2001.
Liu, Hongyong "Motion Track for a Charged Particle in a Uniform Electric Field or a Uniform Magnetic Field", Journal of Sichuan Normal University (Natural Science), vol. 22, No. 4, pp. 438-441, Jul. 1999.

\* cited by examiner

THERAPEUTIC APPARATUS

FIELD OF THE INVENTION

The invention relates to the guiding of charged particles to a target zone within a subject.

BACKGROUND OF THE INVENTION

In charged particle beam therapy, an energetic charged particle beam is directed at a target zone of a subject. The primary mechanism for interaction of a beam comprising charged particles with matter is through the Coulomb force. The cross section for Coulomb collisions increases as the relative velocity of two particles decreases. As a charged particle beam travels through a subject, it loses energy more and more rapidly. The effect of this is that the majority of the energy of the particle beam is deposited near the end of the beam path. There is therefore a large peak of energy deposited at the end of the beam path which is called the Bragg peak.

For this reason, charged particle beam therapy allows very precise delivery of high dose to a tumor target while minimizing the total dose to the patient. However, even small movements of anatomical structures in the path of the beam can lead to significant deviations of the delivered dose from the original dose plan. Therefore, it is desirable to use real-time imaging to track the target and adapt the beam to the motion of organs and of the target.

For charged particle beam therapy, real-time MRI during the delivery of the beam has been unfeasible, because the strong magnetic fields associated with MRI will dramatically impact the path of the charged particles towards the target.

A static magnetic field is used by Magnetic Resonance Imaging (MRI) scanners to align the nuclear spins of atoms as part of the procedure for producing images within the body of a patient. During an MRI scan, Radio Frequency (RF) pulses generated by a transmitter coil cause perturbations to the local magnetic field, and RF signals emitted by the nuclear spins are detected by a receiver coil. These RF signals are used to construct the MRI images. These coils can also be referred to as antennas. Further, the transmitter and receiver coils can also be integrated into a single transceiver coil that performs both functions. It is understood that the use of the term transceiver coil also refers to systems where separate transmitter and receiver coils are used.

U.S. Pat. No. 6,675,078 and corresponding European patent EP 1 121 957 A2 describe a therapeutic apparatus which combines proton beam therapy with MRI. MRI is used for targeting and gating the proton beam therapy.

PCT patent application WO 99/32189 relates to a combined MRI and radiotherapy system. The system described has a magnetic resonance imaging system, a gantry mounted set of coils for generating a magnetic field that rotates with a guiding system for a radiotherapy beam, and it uses MRI to detect the effect of the radiotherapy on an irradiated region.

PCT patent application WO 2006/130659 A2 relates to a method, system, and in particular a computer program product for guiding radiotherapy using an image scanner.

SUMMARY OF THE INVENTION

The invention provides for a therapeutic apparatus and a computer program product for controlling a therapeutic apparatus as claimed in the independent claims. Embodiments of the invention are given in the dependent claims.

Embodiments of the invention address the aforementioned problems by performing the dose planning in a manner that takes trajectory deviations of the charged particles caused by the magnetic field into account and correcting the beam parameters in a way that will direct the proton beam to the target.

In accordance with an embodiment of the invention, the dose planning and beam parameter definition take the magnetic fields of the MRI scanner into account. Knowledge of the fields associated with a Magnetic Resonance (MR) scanner is available based on the magnet design and/or on actual three dimensional (3D) measurements on the final setting of the scanner in the proton beam facility (taking any influence of magnetic material into account which distorts the field further away from the imaging volume). The influence of these fields on the proton path can be calculated. If this calculation is integrated into the dose planning and beam parameter determination software, the protons will deliver the energy at the desired location in the body.

Embodiments of the invention provide for therapeutic apparatus comprising a magnetic resonance imaging system adapted for acquiring a set of magnetic resonance imaging data in the imaging zone, a guiding means adapted for guiding a beam of charged particles to a target zone within a subject, wherein the imaging zone comprises the target zone. The therapeutic apparatus further comprises a zone determination means adapted for determining the location of the target zone within the subject using the set of magnetic resonance imaging data, a trajectory calculation means adapted for calculating a trajectory of the beam using magnetic field data being descriptive of the magnetic field such that the calculated trajectory reaches the target zone, and a control means adapted for controlling the guiding means using the calculated trajectory such that the beam follows the calculated trajectory.

The magnetic resonance imaging system comprises a means for generating a magnetic field. This can be a superconducting magnet. An effect of the large magnetic field used for magnetic resonance imaging is that the magnetic field deflects the trajectory of charged particles in a magnetic field. However, using the magnetic field data, the trajectory of the charged particle beam in the magnetic field can be calculated exactly. This allows the guiding means to guide the beam of charged particles to the target zone within the subject.

The guiding means can guide a beam of charged particles from a particle accelerator. Examples of charged particle accelerators that can be used are a cyclotron, a synchrotron, or a linear accelerator. The guiding means can comprise a system to guide the energetic particles to the magnetic resonance imaging system; the guiding means can also comprise charged particle optics for changing the trajectory of the charged particles that comprise the beam of charged particles. The zone determination means can be implemented as a computer program product that is able to segment the magnetic resonance imaging data and determine the location of the target zone and also of structures within the subject that surround the target zone and lie in the beam path.

The pulse sequences used for acquiring magnetic resonance imaging data can be tailored to locate the target zone, and also to locate high risk organs that can be easily damaged by a charged particle beam. The trajectory calculation means can also be implemented as a computer program product.

The magnetic field data can be magnetic field data that is calculated from a knowledge of the design of the means for generating a magnetic field, or it can be measured directly and stored for later recall, for example in a lookup table. This can be implemented by using magnetic field data and then calculating the trajectory of the charged particles in the beam with small time steps. Essentially, the equation of motion of the particle is integrated in time.

The guiding means can contain charged particle mirrors and also charged plates and objects for deflecting the trajectory of the charged particle beam. To reach the target zone after the trajectory has been calculated by the trajectory calculation means if the beam does not end in the target zone, then the trajectory calculation means can calculate the effect of making an adjustment to the guiding means to see the effect of the trajectory on the charged particle beam. This provides not only a trajectory of the charged particle beam to the target zone, but also the settings necessary for the guiding means for the beam to follow the trajectory to the target zone.

The control means can be implemented as a computer or as a controller and can be adapted for controlling the guiding means such that the trajectory of the beam follows the trajectory that was calculated by the calculation means.

In another embodiment, the guiding means comprises charged particle optics for adjusting the beam trajectory, and an adjustable attenuator for modulating the energy of charged particles comprising the beam. The charged particle optics can be comprised of magnets, electromagnets and also electrodes and structures which can be built up to large voltage potentials. These produce magnetic or electric fields which can be used to deflect or adjust the trajectory of the charged particle beam.

The adjustable attenuator can be implemented as an object which interrupts the path of the charged particles comprising the beam. The charged particles interact predominantly with the matter they travel through using the Coulomb force. As a result, as the velocity of the charged particles becomes slower, their interaction with the surrounding matter becomes more likely. The effect of the attenuator is to reduce the energy of the charged particles comprising the beam. The effect of this is that it reduces the depth to which the charged particle beam can penetrate into the subject. The attenuator can be placed anywhere between the source of the charged particle beam to just before the beam enters the subject. If the attenuator is before or within the guiding means, then the energy of the charged particle beam will change, and this change in energy will need to be accounted for and the guiding means will need to be able to adapt to the change in energy to ensure that the beam of charged particles has the correct trajectory through it.

Placing the attenuator closer to the subject has the advantage that many portions of the guiding means will not need to be adaptable to a changing particle beam energy. A disadvantage is that there is a probability that charged particles such as protons can cause a nuclear reaction which would cause the attenuator to become radioactive. However, this depends upon the type of charged particle being used and also the material which is used as an attenuator.

In another embodiment, the trajectory calculation means is adapted for calculating an energy loss of the charged particles comprising the beam within the subject, and the trajectory calculation means adjusts the calculated trajectory using the energy loss. This is advantageous, because as a charged particle beam passes through matter it gradually loses energy. The energy change will affect the trajectory of charged particles within the magnetic field. The slower the velocity of a particle, the more curvature there will be in a constant magnetic field, and taking this into account allows the trajectory to be calculated accurately.

In another embodiment, the charged particles comprising the beam have a kinetic energy greater than or equal to the kinetic energy necessary so that the Bragg peak of the particle beam is within the target zone. The Bragg peak is the location where the majority of the energy from the charged particle beam is deposited. This embodiment is advantageous, because the charged particles have enough energy to reach the target zone.

In another embodiment, the beam control means further comprises an adjustable attenuator for modulating the location of the Bragg peak of the beam so that the Bragg peak is within the target zone. This embodiment is advantageous, because an attenuator is able to change the energy of the particles comprising the charged particle beam. This effects how far the particles can penetrate into the subject and determines where the majority of energy is deposited. Using an attenuator is advantageous, because the energy of the charged particle beam can be adjusted very rapidly and can be used to compensate for external and internal motion of the subject. Depositing the majority of the energy in the target zone is critical, because the deposition of energy by a particle beam is localized and if the beam is directed to an area outside of the target zone, the subject can be damaged.

In another embodiment, the MRI system is adapted for acquiring the set of magnetic resonance imaging data at periodic intervals. This is advantageous because MRI data can be acquired repeatedly and used to track the motion of the target zone, motion of the subject, and also of internal motion within the subject. In this embodiment the zone determination means is further adapted to monitor motion of the target zone using a set of magnetic resonance imaging data acquired at periodic intervals. This can be implemented by segmentation algorithms which are able to detect the location of the zone determination means and also of surrounding organs which can be damaged by the charged particle beam.

The zone determination means is further adapted to monitor internal motion of the subject along the beam trajectory using the set of magnetic resonance imaging data acquired at periodic intervals. This includes internal motion both perpendicular and parallel to the beam trajectory. This is advantageous, because there can be internal motion within a subject which can affect the trajectory of the particle beam, for instance if the particle beam is traveling through soft tissue or through bony material such as a rib, the attenuation of the particle beam will be different. The trajectory calculation means can then use this information to properly calculate a trajectory which directs the particle beam to the target zone. For this reason the trajectory calculation means is adapted to compensate for motion of the target zone and of the subject along the beam trajectory used during calculation of the trajectory. The interval at which MRI data is acquired is determined by the rate of the movement which should be compensated for. For instance to compensate for the filling of a bladder, MRI data is acquired at a slower rate than if breathing is compensated for.

In another embodiment, the magnetic resonance imaging system is adapted for measuring the trajectory of the charged particles within the image zone. The beam control means is adapted for adjusting the beam trajectory using the measured trajectory. This embodiment it is particularly advantageous, because the magnetic resonance imaging system is able to directly measure the path that the charged particle beam takes. This information is then used by the beam control means to adjust the beam trajectory. This provides verification of the calculated trajectory, and also reduces the chance that areas outside of the target zone of the subject will not be irradiated by the particle beam. The trajectory of the particle beam can be measured by magnetic resonance imaging using several different methods:

Method 1: Use the therapy proton beam as means of MR excitation, by pulsing the beam at the MR Larmor frequency or at a sub-harmonic of the Larmor frequency.

Method 2: Use the de-phasing effect of the Root Mean Square (RMS) beam current in combination with a BOLD-like MR sequence.

Method 3: Use the de-phasing effect due to paramagnetic behavior of beam interaction products.

An estimate showing the viability of detecting a proton beam is made using the following assumptions:

The proton beam is very narrow, with lateral dimensions up to the Bragg zone of less than 1 mm, preferably less than 0.1 mm.

The beam consists of short pulses with a repetition frequency in the range 50-100 MHz and a peak beam current of the order of 100 microampere.

The RMS beam current can reach a level of 0.1 microampere (current levels in clinical therapy systems are 0.01-0.02 microampere).

The duration of the train of proton pulses required for one treatment session is of the order of minutes.

Using these assumptions, the beam current generates a magnetic field circulating around its trajectory. The field drops off with 1/r (r being the distance to the center of the beam). At a radius of 0.1 mm, the B field due to a current of 0.1 microampere is 1.3 nanotesla. For 100 microampere the field at 0.1 mm is 1.3 microtesla.

Example of Method 1

The pulses coming from the proton accelerator have a high and very stable repetition frequency of the order of 100 MHz (this is a design parameter of the cyclotron or synchrotron generating the protons). The MRI system and the proton accelerator can be matched to each other in such a way that the beam pulse repetition frequency is exactly equal to the MR resonance frequency. Then the field around the proton beam acts on the tissue protons as a steady MR excitation pulse. The MR effect of the beam RF field can be switched on and off by either slightly modifying the pulse repetition frequency of the accelerator or by adding a small offset-field to the field of the MR background magnet (using a B0 coil incorporated in the gradient coil system). The MR excitation effect of the beam field can be converted into a visible effect in images in many ways. One way would be to use the beam field as the only MR excitation and to make an image using the resulting MR signal. Such imaging can be performed very rapidly because only voxels very close to the beam will emit signal. In principle, the beam can be reconstructed from three projections. Alternatively, the effect of the beam-related RF field can be used as an RF pre-pulse (such as in an inversion recovery sequence), modulating the signal coming from the voxels through which the beam passes. It is also conceivable to use the beam RF field as a saturation pulse, suppressing the generation of RF signals from the voxels through which the beam passes. The MR excitation effect will also occur if the repetition frequency of the proton pulses is a phase-synchronous sub-harmonic of the Larmor frequency. In general, if the frequency spectrum of the train of proton pulses contains a frequency component at the Larmor frequency, this train of proton pulses will cause MR excitation.

A therapeutic apparatus adapted to image the beam may have one or more of the following design features:

Identical frequencies for MR resonance and proton beam pulse repetition

Accurate frequency lock between the sub-systems.

A means to switch between MR resonance and off-resonance by either modulating the accelerator frequency or the total B0 field of the MR scanner.

Example of Method 2

The RMS beam current generates an RMS magnetic field around the beam which modulates the resonance frequency in the voxels through which the beam passes. At an average beam current of 0.1 microamperes, the frequency offset at 0.1 mm from the center of the beam is about 0.05 Hz. Using a MR detection method such as Blood Oxygen Level Dependent (BOLD) contrast functional imaging, this frequency offset can be visualized. Visualizing the beam using this method will involve periodically interrupting the transmission of the proton beam and to compare MR images with and without the proton beam being transmitted. In order to enhance the visibility of the proton beam the RMS beam current can be increased during the time when the MR de-phasing effect is required. For example, the average current can be kept at a level of 0.02 microampere for most of the time (the current practical clinical level) but increased to 0.2-1.0 microampere in intervals between the RF excitation pulse and the start of the MR acquisition window. In this case, the duty cycle of the enhanced amplitude part of the beam current could be of the order of 5%. Such a limited high-amplitude operation of the proton delivery system is probably acceptable if the current is being limited by heating of components.

Example of Method 3

The protons will result in ionization of the tissue. The free radicals thus formed will be paramagnetic and will result in a local decrease in the T2 relaxation time of the tissue. This effect can therefore be visualized using T2 sensitive imaging sequences.

In another embodiment, the charged particle beam comprises at least one of the following: protons, carbon nuclei, or atomic nuclei. The use of protons, carbon nuclei or another atomic nuclei is beneficial, because with their large mass they will be able to penetrate into a subject if the charged particle beam has sufficient energy.

In another embodiment, the zone determination means is further adapted for receiving planning data for planning therapy. The zone determination means is also adapted for confirming if the planning data satisfies a predetermined criterion using a set of magnetic resonance imaging data. When therapy is performed with a charged particle beam, a physician will normally take three-dimensional images of the subject using a medical imaging system such as magnetic resonance imaging or computer tomography with X-ray and then plan the treatment of the subject based on this three-dimensional data. This embodiment has the advantage that the zone determination means confirms if the planning data satisfies a predetermined criterion and determines if the anatomy of the subject is indeed close to the anatomy that was used when the planning data was generated.

Due to the large cost of particle accelerators it is possible that the planning data can be generated at a site using a different medical imaging system which is part of the therapeutic apparatus. Also the internal anatomy of the subject could have changed since the planning was performed by the physician. For example the person could have more fat, or in the case of treating a prostate the latter could be filled with more liquid or less liquid than it was during the planning. The planning data can be verified by comparison with a predetermined criterion. If the planning data does not satisfy a predetermined criterion, at least one of the following actions can be performed: halting the generation of the beam of charged particles, alerting an operator that the planning data is not accurate, adjusting the planning data, or receiving corrections to the planning data from the operator. If the planning data is not accurate then it is beneficial to halt the generation of the beam of charged particles, because this prevents the charged particles from traversing a region of the subject that was not intended. Alerting an operator that the planning data is not accurate is advantageous, because the operator then knows that there is sufficient discrepancy between the anatomy of the subject and the anatomy used during planning that the treatment will not proceed properly. The zone determination means can be implemented using segmentation algorithms and the planning data can be adjusted using the segmented MRI images. This is advantageous, because small changes in the anatomy can be compensated for automatically by the system. In addition, movement and breathing can be compensated for in the treatment plan. For instance, the movement of ribs in and out of the beam path due breathing can cause errors during therapy. However using the MRI images this movement can be accounted for and the treatment plan can be adjusted.

Receiving corrections to the planning data is advantageous, because a skilled operator or physician can then manually make corrections to the planning data.

In another embodiment the means for generating the magnetic field comprises a split magnet comprising two cylindrical sub-magnets. This embodiment is advantageous, because the particle beam can be directed between the two cylindrical sub-magnets and also magnetic resonance imaging data can be acquired in the region between the two cylindrical sub-magnets. However, the imaging volume is not necessarily limited to the region between the two cylindrical sub-magnets, because the imaging volume can also extend along the axis of symmetry of the cylindrical sub magnets into the region surrounded by the two cylindrical sub magnets.

In another embodiment, the means for generating a magnetic field comprises a split magnet comprising at least two cylindrical sub-magnets wherein the axis of cylindrical symmetry of the two sub-magnets are aligned and the mid-plane of the split magnet divides the at least two sub-magnets, wherein the split magnet has a central region about its axis, a cylindrical symmetry wherein the imaging zone lies within the central region and is centered on the mid-plane, and wherein there is a split zone between the two sub-magnets, wherein the guiding means are adapted such that the beam traverses the split zone wherein the guiding means is adapted for rotation about the axis of cylindrical symmetry of the split magnet. This embodiment is advantageous, because the magnetic field between the at least two cylindrical sub-magnets will be uniform enough to acquire magnetic resonance imaging data and there will also be clearance for the particle beam between the two cylindrical sub-magnets.

In another embodiment, the radio frequency coil of the magnetic resonance system is split along the mid-plane of the split magnet. This is advantageous because it enables the traversal of the beam to the target zone.

In accordance with an embodiment of the invention the radio-frequency coil of the magnetic resonance system is split along the mid-plane of the split magnet to enable the traversal of the beam to the target zone.

In accordance with an embodiment of the invention, the gradient coil of the magnetic resonance system is split along the mid-plane of the split magnet to enable the traversal of the beam to the target zone.

In accordance with an embodiment of the invention, the two sub magnets are interconnected, preferably the two sub magnets being connected with at least two cold supports. Cold supports are adapted for providing a rigid mechanical and a superconducting, electrical connection between the two sub magnets.

In accordance with an embodiment of the invention, the therapeutic apparatus further comprises a subject support for supporting a subject, and wherein the cold supports are positioned in an angular arrangement that is not mirror symmetric with respect to the sagittal or coronal symmetry planes of the imaging zone.

In another embodiment, the guiding means further comprises a beam guide adapted to guide a beam from a charge particle generation means and the beam guide is adapted for rotation around the axis of symmetry of the split magnet. This embodiment is advantageous, because the beam guide is rotated around the axis of symmetry of the split magnet, this design feature has the effect that as the beam guide is rotated the magnetic field that charge particles experience when traveling through the beam guide does not change.

In accordance with an embodiment of the invention, the beam guide has at least first, second, and third bending magnets, wherein the first bending magnet is located in the symmetry plane of the magnet, wherein the second bending magnet is located at the axis of symmetry of the split magnet, and wherein the third bending magnet is located along the path of the beam between the first and second bending magnets, preferably at a distance of less than 2 meters from the mid-plane of the magnet.

In another embodiment, the split magnet comprises a subject tunnel adapted for receiving a subject, wherein the therapeutic apparatus clearly comprises a subject support for supporting the subject, wherein a subject support is located within the subject tunnel, wherein the guiding means further comprises a beam pipe, wherein the beam pipe comprises an evacuated tube and wherein the beam pipe extends from the guiding means to the surface of the subject tunnel. This embodiment is advantageous, because an evacuated beam pipe does not contain air which can be ionized or take energy from the particle beam.

In another embodiment, the split magnet has shielding coils for reducing the stray magnetic field of the split magnet and wherein the shielding coils are arranged so that there is a region of zero magnetic field surrounding the split magnet, which is used to reduce the effect of the magnetic field of the split magnet on the charged particle optics. This is advantageous, because the charged particle optics can contain various materials which are used to generate magnet field which is used to deflect the particle beam.

The magnetic field can impair the operation of the charged particle optics. By providing a region of low or zero magnetic field, it is easier and costs less to develop charged particle optics which are adapted for adjusting the trajectory of the charged particle beam.

By a region of zero magnetic field, it is understood that the magnetic field is so low that for all intents and purposes it does not affect the trajectory of the particle beam. Due to defects in the manufacture or in the design of the magnet there may be low fields in this region, and there also may be magnetic fields due to the earth. However, by the proper placement of shielding coils a region can be created around the magnet which has a very low magnetic field. Also around this region the magnetic field is lower than in other areas surrounding the magnet. In the region surrounding the region of zero magnetic field, the effect of the magnetic field on the charged particles is also therefore reduced.

In another aspect, the invention provides for a computer program product for controlling a therapeutic apparatus. The computer program product comprises executable instructions for performing the steps of acquiring a set of magnetic resonance imaging data using a magnetic resonance imaging system, and guiding a beam of charged particles using a guiding means to a target zone within the subject. The imaging zone comprises the target zone. The instructions for performing the steps further comprise determining the location of the target zone using a zone determination means using said magnetic resonance imaging data, calculating the trajectory of the beam using a trajectory calculation means using magnetic field data being descriptive of the magnetic field such that the calculated trajectory reaches the target zone, and firing the beam at the target zone using a charged particle generation means. It is advantageous to have a computer program product control such as therapeutic apparatus, because the computer can control the apparatus and perform necessary calculations faster than a human could. Further advantages of this computer program product are analogous to the previously described therapeutic apparatus.

In another embodiment, the computer program product comprises executable instructions further comprising performing the steps of calculating an energy loss of the beam within a subject and adjusting the calculated trajectory using the energy loss. The advantage of this has been previously discussed.

In another embodiment, the computer program product further comprises executable instructions for performing the steps of acquiring a set of magnetic resonance imaging data using the magnetic resonance imaging data at periodic intervals at a rate fast enough to monitor subject motion, monitoring the motion of the target zone and of internal motion of the subject along the beam trajectory with the zone determination means using a set of magnetic resonance imaging data acquired at periodic intervals, calculating the trajectory of the beam using the trajectory calculation means using the magnetic field data such that the motion of the target zone and of the internal motion of the subject along the beam trajectory is compensated for, guiding a beam of charged particles using the guiding means to a target zone within the subject and controlling the beam trajectory with the control means in order to correct for motion of the target zone and other subjects along the beam trajectory. Again this is advantageous because this can be performed more rapidly and efficiently by a computer than can be performed by a human. The advantages of this are also analogous to those previously described for the therapeutic apparatus.

In another embodiment, the executable instructions further comprise performing the steps of measuring the trajectory of the charged particles within the imaging zone using the magnetic resonance imaging system and adjusting the direction of the beam with the beam control means using the measured trajectory. The advantages and the method of this have been previously discussed.

In another embodiment, the computer program product further comprises executable instructions for performing the steps of receiving planning data for planning therapy using the therapeutic apparatus, confirming if the planning data satisfies a predetermined criteria using a set of magnetic resonance imaging data, performing at least one of the following if the planning data does not satisfy the predetermined criteria: halting generation of the beam of charged particles, alerting the operator that the planning data is not accurate, adjusting the planning data, or receiving corrections to the planning data from the operator. The advantage of this has been previously discussed.

BRIEF DESCRIPTION OF THE DRAWINGS

In the following preferred embodiments of the invention will be described, by way of example only, and with reference to the drawings in which.

DETAILED DESCRIPTION

Figure 1:
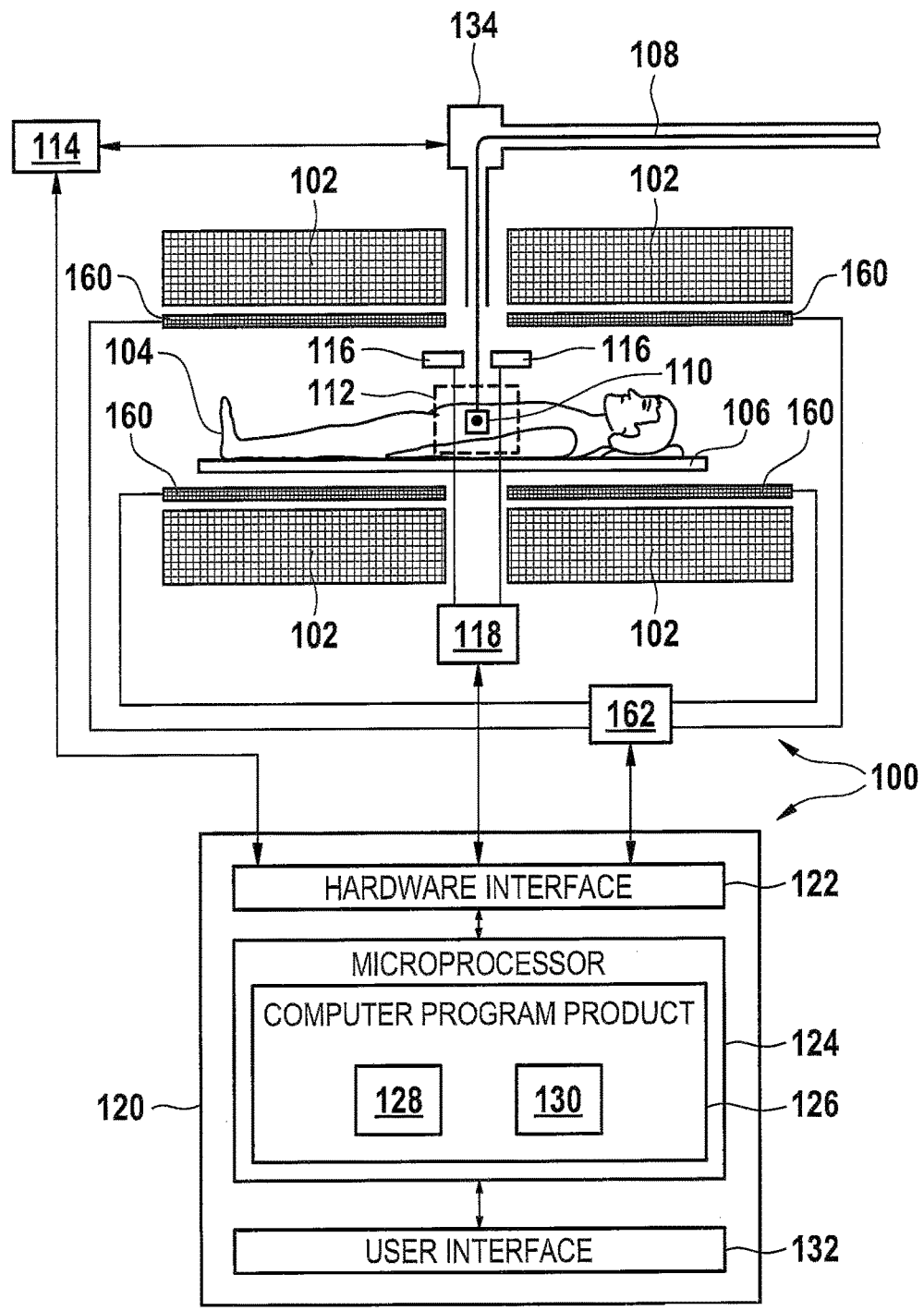
FIG. 1 shows an idealized, cross sectional view of an embodiment of a therapeutic apparatus according to an embodiment of the invention.
Figure 2:
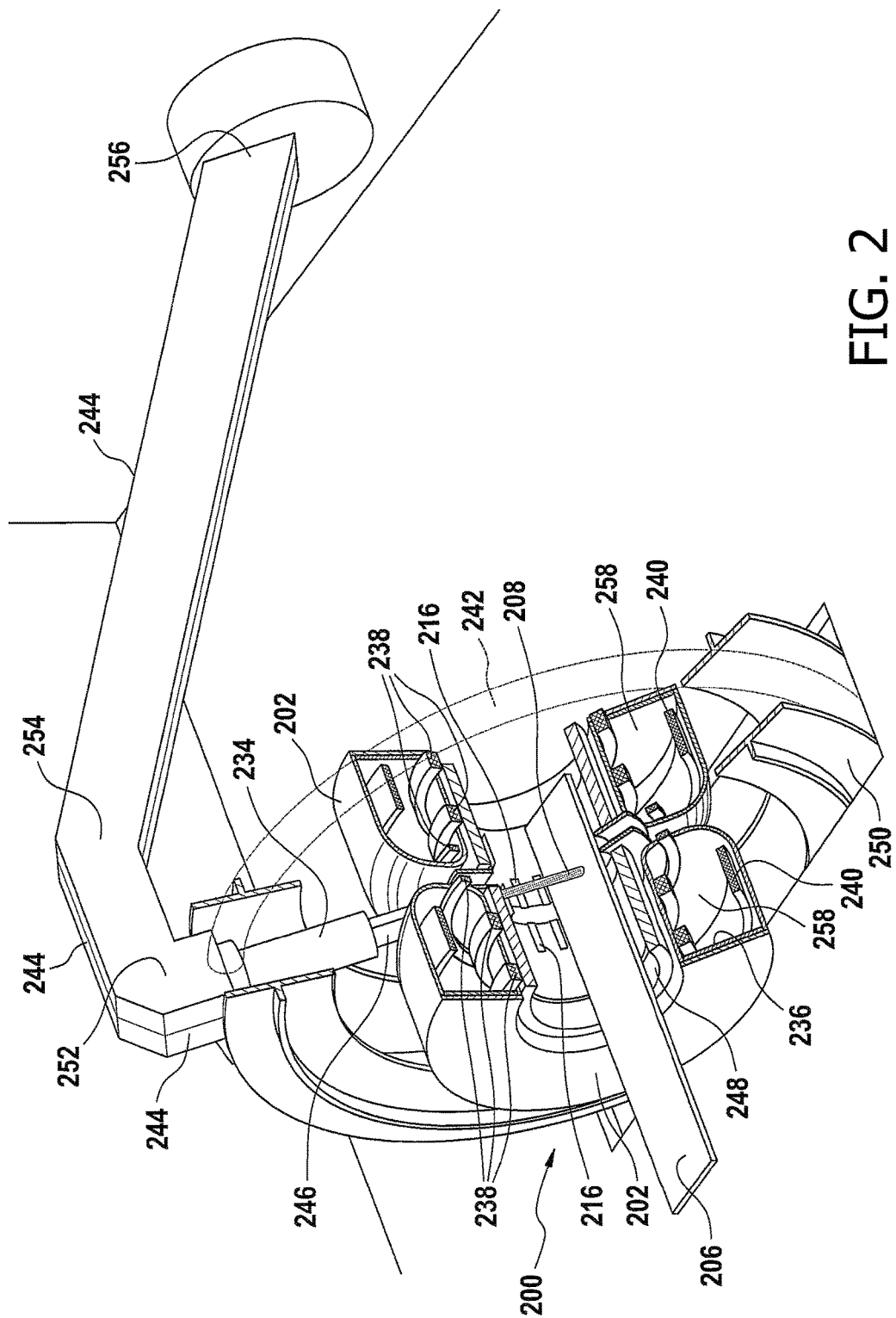
FIG. 2 shows a sectioned, perspective view of an embodiment of a therapeutic apparatus according to an embodiment of the invention.

Elements in FIG. 1 and FIG. 2 that are either identical elements or perform the same function are numbered such that the last two digits are identical. Elements FIG. 2 which have been described in FIG. 1 will not necessarily be discussed again if the function is identical.

FIG. 1 shows an idealized cross-sectional view of an embodiment of a therapeutic apparatus according to an embodiment of the invention. This figure shows a magnetic resonance imaging system 100 that comprises a split magnet that is comprised of two sub-magnets 102. Within the bore of the sub-magnets 102, there is space for a subject support 106 adapted for receiving a subject 104. Between the two sub-magnets 102, there is an imaging zone 112 where the magnetic field is uniform enough that magnetic resonance imaging data can be acquired. Within the imaging zone 112 there is a target zone 110. Magnetic resonance imaging data is acquired using a split transceiver coil 116 in this embodiment. Spatial encoding of the information is performed by means of a split gradient coil 160. In this embodiment, the gradient coil 160 is located within the bore of the magnet 102.

In this embodiment, the split transceiver coil 116 is set directly on the subject 104. In other embodiments the coils used for acquiring magnetic resonance imaging data can be mounted within the bore of the magnet 102, they can be mounted on supports, or they can be mounted to the gradient coil 160. The magnetic resonance imaging data is used to guide the particle beam 108, so it is necessary that the position of the gradient coil 160 is known relative to the guiding means 134.

The transceiver coil 116 is connected to a transceiver 118. The transceiver is able to emit and also receive radio frequency signals. The transceiver then interfaces with a computer 120 via a hardware interface 122. The gradient coil is powered by a gradient amplifier 162 which is controlled via the hardware interface 122. The gradient amplifier 162 is a power amplifier capable of supplying the gradient coils 160 with current. The computer has a microprocessor 124 which has a computer program product 126 which is adapted for constructing images from the data obtained by the transceiver 118. The computer program product 126 also comprises a zone determination means 128 and a trajectory calculation means 130.

The zone determination means 128 can be implemented as a segmentation module which is adapted for segmenting the anatomical regions of the MRI images. The trajectory calculation means can be implemented using magnetic field data which describes the magnetic field surrounding the magnet and also a particle integrator for integrating the equations of motion of the position of the particle in small time steps. The computer also comprises a user interface 132 which is adapted for receiving instructions from an operator. The hardware interface 122 of the computer 120 also is connected to the control means 114. The control means 114 is adapted for controlling the guiding means 134. The guiding means 134 is adapted for directing a particle beam 108 to the target zone 110. In this embodiment the transceiver coil 116 and the gradient coil 160 have a split design so that the particle beam does not intersect the transceiver coil 116 or the gradient coil 160.

FIG. 2 shows a section perspective view of an embodiment of a therapeutic apparatus according to an embodiment of the invention. The MRI system 200 in this embodiment comprises a split magnet comprised of two sub-magnets 202. There is a subject tunnel 248 adapted for receiving a subject. In this embodiment, the subject tunnel 248 comprises the gradient coil. The gradient coil can be embedded within the subject tunnel. In other embodiments, the gradient coil and the subject tunnel can be separate. Embedding gradient coils in the subject coil clearly defines the position of the gradient coils relative to the guiding means 134, so the location of MRI images is clearly defined relative to the guiding means 134.

Within the subject tunnel 248 is a subject support 206 adapted for receiving a subject. Each sub-magnet 202 is comprised of a radiation shielding 236 and a cryogenic chamber 258. Within the cryogenic chamber 258 are superconducting coils 238 and a superconducting shielding coil 248 adapted for generating a magnetic field. The superconducting shielding coil 248 is adapted such that there is a region of zero magnetic field 242 surrounding the sub-magnet 102. The pulsed electromagnets used to scan the proton beam are preferably located inside this low-field ring 242; this allows the use of efficient scanning magnets with a ferromagnetic return yoke.

Between the two sub-magnets 202 there is space which a beam pipe 246 and a beam of charged particles 208 can traverse. There is a rotatable support surrounding the MRI system 200. The rotatable support holds a beam guide 244 and the guiding means 234. The guiding means 234 is adapted for adjusting the trajectory of the particle beam 208. The beam pipe 246 is an evacuated tube which is adapted to allow the particle beam 208 to pass through. In this embodiment, it does not extend into the subject tunnel 248.

The beam guide 244 is adapted for guiding a particle beam 208 from a charged particle source to the guiding means 234. In this embodiment the beam guide 244 is able to rotate at exactly the axis of symmetry of the MRI system 200. This has the advantage that as the beam guide 244 and also the guiding means 234 rotate around the sub-magnets 202, the magnetic field that particles feel does not change. This has the advantage that as the beam guide 244 and guiding means 234 are rotated that they can be moved without having to compensate for changes in the magnetic field. As the rotatable support 250 is rotated around the MRI system 200, the particle beam 208 will take a different trajectory into a subject. The subject support 206 is also adapted for motion during therapy. By adjusting the patient support 206 the rotatable support 250 and controlling the guiding means 234 any region of the subject can be treated with the particle beam 208.

The beam guide 244 is also comprised of a first bending magnet, a second bending magnet and a third bending magnet. In this embodiment it can be seen that the first bending magnet is located 252 in the plane between the two sub-magnets 102. The beam guide then extends away from the two sub-magnets where the second bending magnet is located 254. The third bending magnet is then located 256 such that the beam is bent at the axis of symmetry of the MRI system 200.

Although the stray field of the MRI magnet can be made small at distances greater than 3 meters from the iso-center, the remaining fields can be large enough to cause unacceptable deflection of the charged particle beam along the beam guide 244 between the swivel point and the 90 degree bending magnet. In order to compensate for this stray field, the beam guide 244 is preferably actively shielded by means of an assembly of permanent magnets and/or electromagnets, distributed along the beam guide 244. The distribution and strength of these compensation magnets can be such that the component of the magnetic field in the plane through the beam path and the iso-center of the magnet and perpendicular to the beam path is cancelled. The influence of the stray field of the sub magnets 202 can also be reduced by using at least two bending magnets, which allows locating the beam guide 244 further away from the high-field zone of the MRI magnet.

The two sub magnets 202 can be interconnected by at least two cold support members, with appropriate cryogenic insulation. The angular position of these support members can be chosen such that no interference occurs with the required rotation of the proton beam system to provide a free aperture of at least 90 degrees between adjacent support elements.

The gradient coil, embedded in the subject tunnel in this embodiment 248, used in the split MRI system can be similar in design to the gapped gradient coil for an integrated whole body PET/MR system. A key characteristic of this type of gradient coil is that the flanges on either side of the central gap carry conductors belonging to the x and y gradient coils, which may interconnect conductors on the inner surface of the coil and conductors on the outer surface of the coil structure. In contrast to the PET/MR gradient coil, the two halves of the coil of the therapeutic apparatus cannot be interconnected by a closed thin-walled central cylinder, since such a cylinder would block the proton beam. Instead, each of the two halves of the coil can be separately mounted in the magnet system. Since the magnet is also nearly completely split (except for any interconnecting posts), the magnet has stiff mounting surfaces close to the central gap, which can advantageously be used to react the lateral forces on the gradient coil. Alternatively, the gradient coil halves can be mounted to the floor by means of a mounting structure located in the lower part of the magnet gap assuming that the allowed angular positions of the proton beam system will be restricted to the region above the horizontal symmetry plane of the system. However, in order to avoid radioactive activation of system components, it is preferable to avoid construction material in the gap of the magnet as much as possible.

In order to avoid RF coupling between the transceiver coil 216 and the gradient coil, which would seriously degrade the quality factor of the transceiver coil 216, MR systems generally feature an RF shield covering the inner surface of the gradient coil. Because of the split in the gradient coil, it is necessary to extend this cylindrical RF shield over the flanges of the gradient coil facing the central gap, preferably in such a way that the shield makes electrical contact with the bore of the magnet. The rungs of the transceiver coil 216 (which may be a birdcage or TEM resonator) can be split such that these do not cross the central gap. Each of the half-rods may be electrically connected to the flange part of the RF shield, either directly or by means of capacitors.

The zero magnetic field zone 242 surrounding the sub magnets 202 can advantageously be used to locate components of the proton beam system which are magnetic. Magnetic material located in this zone does not become magnetized and hence does not lead to distortion of the magnetic field inside the MRI scanner. The low magnetic field region 242 can also be used to locate parts of the proton beam system which would stop working when exposed to a magnetic field. Examples are devices having a high-permeability magnetic shield, field sensitive sensors and transducers or high-vacuum components.

Figure 3:
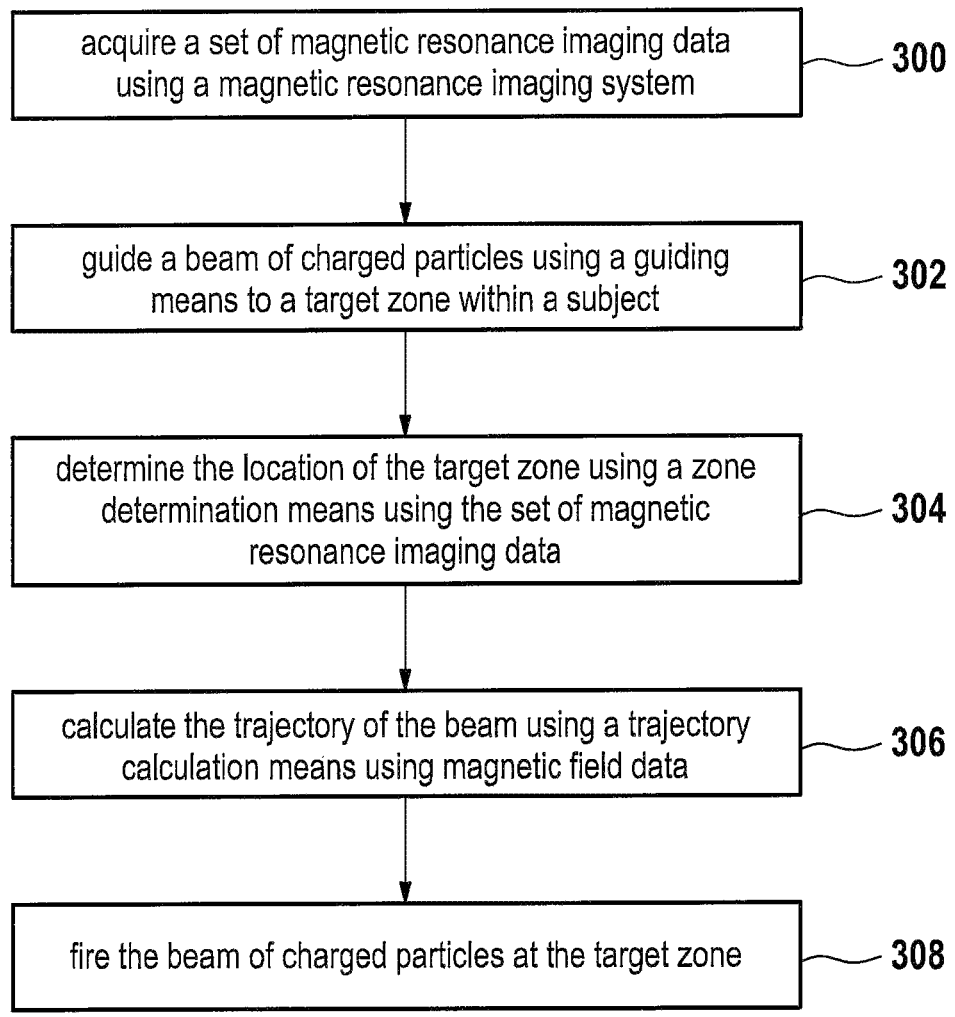
FIG. 3 shows an embodiment of the steps of a computer program product for controlling a therapeutic apparatus according to an embodiment of the invention.

FIG. 3 shows an embodiment of the steps of a computer program product for controlling a therapeutic apparatus according to an embodiment of the invention. The first step is acquiring a set of magnetic resonance imaging data using a magnetic resonance imaging system 300. The second step is to guide a beam of charged particles using the guiding means to a target zone within the subject 302. The third step is determining the location of the target zone using a zone determination means using the set of magnetic resonance imaging data 304. The fourth step is calculating the trajectory of the beam using a trajectory calculation means using magnetic field data 306. Finally, the beam of charged particles is fired at the target zone 308.

Figure 4:
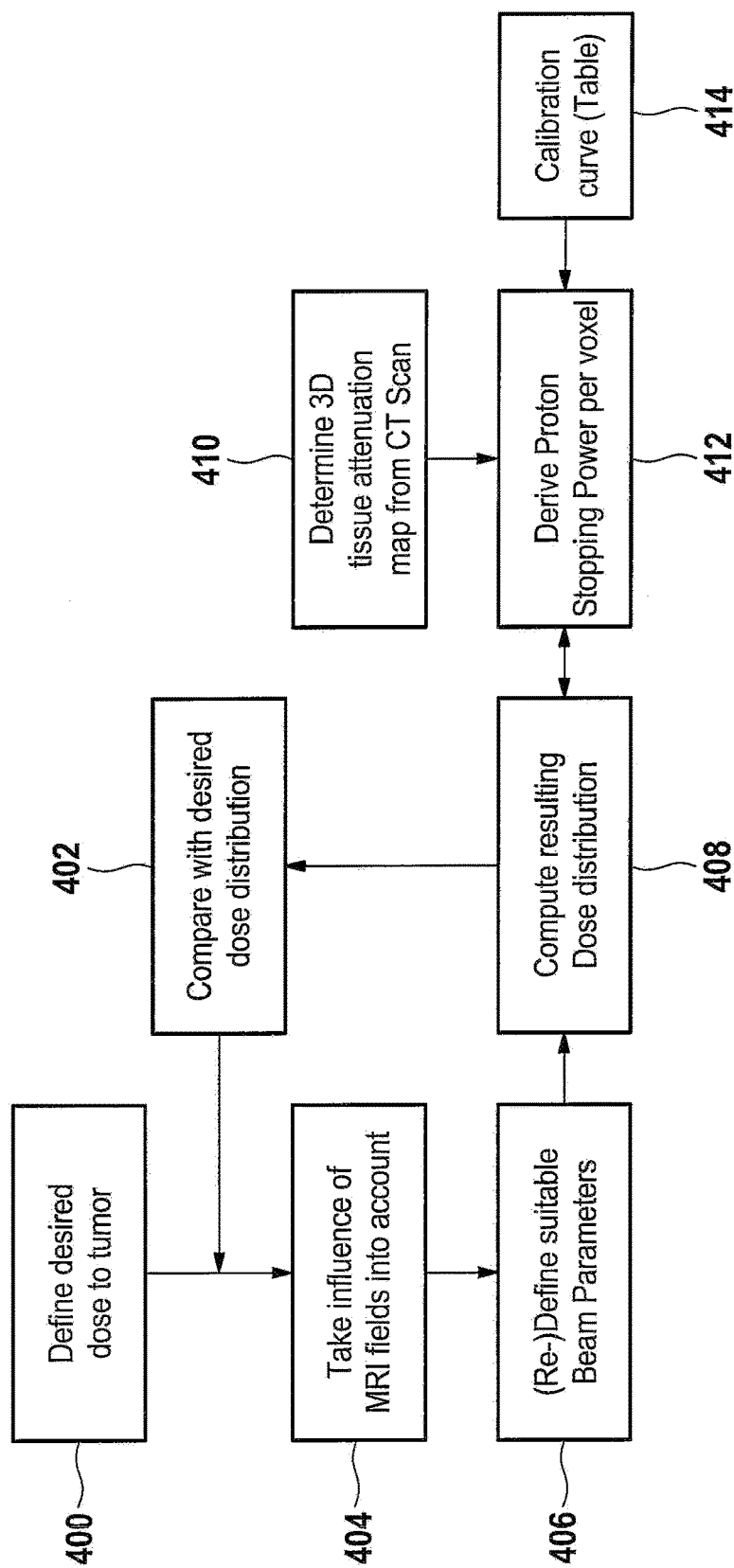
FIG. 4 shows an embodiment of the steps of a computer program product for controlling a therapeutic apparatus according to an embodiment of the invention.

FIG. 4 shows an embodiment of the steps of a computer program product for controlling a therapeutic apparatus according to an embodiment of the invention. The steps comprise defining the desired dose to tumor 400. This would be the receiving of a desired dose plan from a physician or skilled operator. Next the magnetic fields around the magnetic resonance imaging system are taken into account when calculating the trajectory of charged particles going to the tumor 404. The beam parameters are computed such that the dose deposition in the target is achieved with beams which have a curved path instead of straight lines. Next the suitable beam parameters are either defined or redefined 406. These are the parameters used for controlling the trajectory of the beam. From this, the dose distribution is computed 408. The dose distribution is computed using additional information which may be gained from a 3D tissue attenuation map using a CT scanner 410.

Using this tissue attenuation map, the proton stopping power per voxel is derived 412. This is also done with a calibration curve or table 414 that is able to correlate the data from the CT scan and determine the proton stopping power. This information is then used while computing the resulting dose distribution 408. The computed dose distribution is then compared with the desired dose distribution 402. If the desired dose distribution 402 does not meet a predetermined set of criteria then the process starts again. This process is repeated iteratively until the computed dose distribution is sufficiently close to the defined dose distribution.

Figure 5:
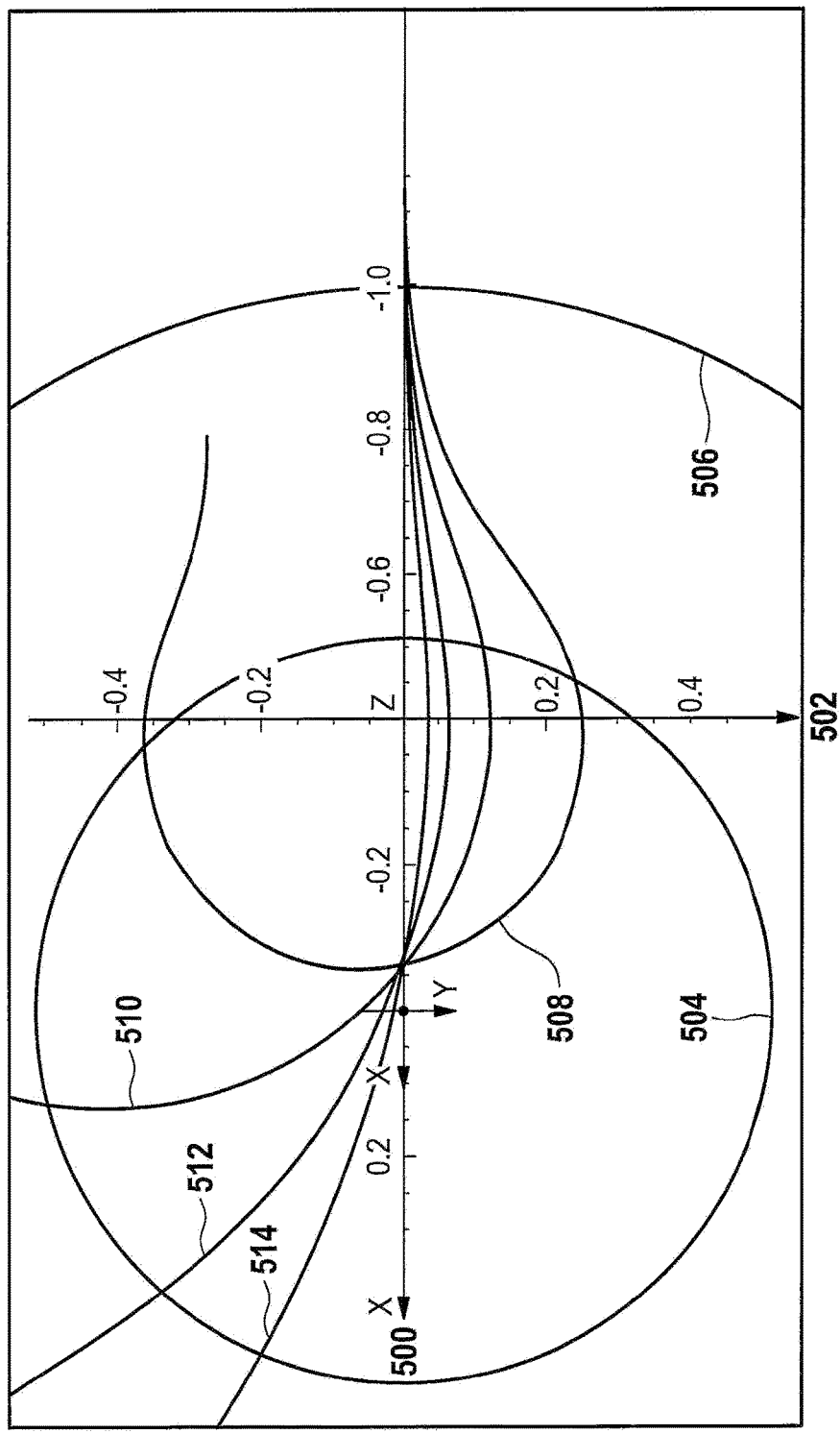
FIG. 5 shows calculated proton beam trajectories in the field of a 1.5 Tesla magnetic resonance imaging system.

FIG. 5 shows a calculated proton beam trajectories in the field of a 1.5 Tesla magnetic resonance imaging system. This is a cross-sectional view of the magnet and it is assumed that this is the space between a split magnet MRI system. The x-axis 500 defines the distance from the axis of symmetry of the magnet and the y-axis 502 defines the distance from the center of the axis of symmetry. The z-axis lies along the axis of symmetry. This figure shows the inner diameter of the magnet 504 and the outer diameter of the magnet 506. The magnetic fields are not shown in this figure only the trajectories. This figure shows the trajectory of a 10 MeV proton 508, a 30 MeV proton 510, a 100 MeV proton 512, and a 300 MeV proton 514.

FIG. 5 demonstrates how significantly charged particle trajectories paths deviate from the straight line which they follow in the absence of a magnetic field. The calculations in this figure show that for these energies, the paths can be used for therapy, especially when taking into account that the deeper the target is located in the subject, the higher the energy which will be used for the therapy. This means that in all practical cases, the actual path length in the subject, along which energy will be deposited, is only slightly longer in the presence of the magnetic field than for the straight paths encountered in the absence of the MRI system.

The relativistic calculations shown in FIG. 5 do not take into account the energy loss along the path into account. After penetrating into the body, the energy of the protons gradually decreases to zero and in the magnetic field of the MR scanner, this results in a decreasing radius of curvature of the proton path inside the body. However, the proton energy as a function of the position of the path inside the patient is known with high precision, as this information is also needed to determine the position of the Bragg-peak, where the major therapeutic effect takes place. The exact curvature of the beam is therefore exactly predictable, both inside and outside the patient. Note that the proton energy decreases from 30 MeV to zero over a distance of typically 10 mm, so that the part of the proton trajectory with large curvature remains small.

LIST OF REFERENCE NUMERALS

100 Magnetic resonance imaging system
102 sub magnet
104 Subject
106 Subject support
108 Beam of charged particles
110 Target zone
112 Imaging zone
114 Control means
116 Split transceiver coil
118 Transceiver
120 Computer
122 Hardware interface
124 Microprocessor
126 Computer program product
128 Zone determination means
130 Trajectory calculation means
132 User interface
134 Guiding means
160 Gradient coil
162 Gradient amplifier
200 Magnetic resonance imaging system
202 sub magnet
206 Subject support 208 Beam of charged particles
216 Split transceiver coil
234 Guiding means
236 Radiation shielding
238 Superconducting coil
240 Superconducting shielding coil
242 Region of zero magnetic field
244 Beam guide
246 Beam pipe
248 Subject tunnel
250 Rotatable support
252 Location of first bending magnet
254 Location of second bending magnet
256 Location of third bending magnet
258 Cryogenic chamber
300 Acquire a set of magnetic resonance imaging data using a magnetic resonance imaging system
302 Guide a beam of charged particles using a guiding means to a target zone within a subject
304 Determine the location of the target zone using a zone determination means using the set of magnetic resonance imaging data
306 Calculate the trajectory of the beam using a trajectory calculation means using magnetic field data
308 Fire the beam of charged particles at the target zone
400 Define desired dose to tumor
402 Compare with desired dose distribution
404 Take influence of MRI field into account
406 (Re-)Define suitable beam parameters
408 Compute resulting dose distribution
410 Determine 3D tissue attenuation map from CT scan
412 Derive Proton Stopping Power per voxel
414 Calibration curve (Table)
500 Distance from center of magnet for x coordinate
502 Distance from center of magnet for y coordinate
504 Inner diameter of magnet
506 Outer diameter of magnet
508 Trajectory of 10 MeV proton
510 Trajectory of 30 MeV proton
512 Trajectory of 100 MeV proton
514 Trajectory of 300 MeV proton

The invention claimed is:

1. A therapeutic apparatus, comprising:
a magnetic resonance imaging (MRI) system for generating a magnetic field and magnetic field data descriptive of the magnetic field, and for acquiring MRI data in an imaging zone;
a guide for a guiding a beam of charged particles for therapy along a path, through the magnetic field, which directs the beam of charged particles for therapy to a target zone within a subject, wherein the target zone is within the imaging zone;
a zone locator for using the MRI data to determine a location of the target zone within the subject;
a trajectory calculator for calculating, using the magnetic field data, a calculated trajectory of the beam of charged particles for therapy along the path, through the magnetic field, which directs the beam of charged particles for therapy to the target zone,
wherein the MRI system is further configured to measure an actual trajectory of the beam of charged particles for therapy within the imaging zone using the MRI data; and
a controller configured to control the guide in response to the actual trajectory measured by the MRI system to guide the beam of charged particles for therapy to follow the calculated trajectory.

2. The therapeutic apparatus of claim 1, wherein the guide comprises
charged particle optics for adjusting the path; and
an adjustable attenuator for modulating the energy of the charged particles of the beam.

3. The therapeutic apparatus of claim 1, wherein the trajectory calculator calculates an energy loss of the beam charged particles for therapy within the subject, and adjusts the calculated trajectory using the energy loss.

4. The therapeutic apparatus of claim 3, wherein the beam of charged particles for therapy includes charged particles that have a kinetic energy greater than or equal to the kinetic energy necessary for the Bragg-peak of the particle beam to be within the target zone, and
further comprising an adjustable attenuator for modulating the location of the Bragg-peak of the beam so that the Bragg-peak is within the target zone.

5. The therapeutic apparatus of claim 1, wherein the MRI data is acquired at periodic intervals, the zone locator further configured using the MRI data to monitor internal motion of the subject along the path, and the trajectory calculator is further configured to compensate for the internal motion of the subject during calculation of the calculated trajectory.

6. The therapeutic apparatus of claim 1, wherein the beam of charged particles for therapy comprises at least one of the following: protons, carbon nuclei, or atomic nuclei.

7. The therapeutic apparatus of claim 1, wherein the zone locator receives planning data for planning therapy, confirms when the planning data satisfies a predetermined criterion using the MRI data, and when the planning data does not satisfy the predetermined criterion performs at least one of: halting the generation of the beam of charged particles for therapy, alerting an operator that the planning data is not accurate, adjusting the planning data, and receiving corrections to the planning data from the operator.

8. The therapeutic apparatus of claim 1, further comprising a split magnet having at least two cylindrical sub magnets for generating the magnetic field, the axes of cylindrical symmetry of the two sub magnets are aligned and the mid-plane of the split magnet divides the two sub magnets, the split magnet has a central region about its axis of cylindrical symmetry, and a split zone between the two sub magnets and the imaging zone lies within the central region and is centered on the mid-plane,
wherein the beam of charged particles for therapy traverses the split zone, and the guide rotates about the axis of cylindrical symmetry of the split magnet.

9. A method for controlling a therapeutic apparatus including a magnetic resonance imaging (MRI) system, the method:
generating a magnetic field and magnetic field data descriptive of the magnetic field;
acquiring MRI data in an imaging zone;
determining a location of a target zone within a subject using the MRI data, wherein the target zone is located within the imaging zone;
calculating a calculated trajectory of a beam of charged particles for therapy along a path through the magnetic field which directs the beam of charged particles for therapy to the target zone using the magnetic field data;
using the MRI data to measure an actual trajectory of the beam of charged particles for therapy; and
in response to the actual trajectory measured using the MRI data, guiding the beam of charged particles for therapy along the path, through the magnetic field, which directs the beam of charged particles for therapy to the target zone by controlling the beam of charged particles for therapy to follow the calculated trajectory.

10. The method of claim 9, further comprising:
calculating an energy loss of the beam of charged particles for therapy within the subject, and
adjusting the calculated trajectory using the energy loss.

11. The method of claim 9, further comprising:
acquiring the MRI data at periodic intervals at a rate fast enough to monitor subject motion;
monitoring, using the MRI data, internal motion of the subject along the path; and
compensating for the internal motion of the subject during calculation of the calculated trajectory.

12. The method of claim 9, further comprising controlling the beam to follow the calculated trajectory in order to correct for motion of the target zone and of the subject.

13. A computer readable non-transitory medium for storing computer readable code, which when executed by a computer performs a method of controlling a therapeutic apparatus including a magnetic resonance imaging (MRI) system, the method comprising acts of:
generating a magnetic field and magnetic field data descriptive of the magnetic field;
acquiring MRI data in an imaging zone;
determining a location of a target zone within a subject using the MRI data, wherein the target zone is located within the imaging zone;
calculating a calculated trajectory of a beam of charged particles for therapy along a path, through the magnetic field, which directs the beam of charged particles for therapy to the target zone using the magnetic field data;
using the MRI data to measure an actual trajectory of the beam of charged particles for therapy; and
in response to the actual trajectory measured using the MRI data, guiding the beam of charged particles along the path, through the magnetic field, which directs the beam of charged particles for therapy to the target zone by controlling the beam of charged particles for therapy to follow the calculated trajectory.

14. The system of claim 1, wherein a pulse repetition frequency of the beam of charged particles for therapy is exactly equal to a resonance frequency of an MR signal generated by the MRI system from which the MRI data is acquired.

15. The system of claim 1, wherein the MRI system is configured to measure the actual trajectory of the beam of charged particles for therapy using the MRI data by performing Blood Oxygen Level Dependent (BOLD) contrast functional imaging to detect a modulation of a resonance frequency in voxels through which the beam of charged particles for therapy passes which is produced by a root mean square (RMS) magnetic field around the beam of charged particles for therapy.

16. The system of claim 1, wherein the MRI system is configured to measure the actual trajectory of the beam of charged particles for therapy using the MRI data by measuring a local decrease in T2 relaxation time of tissue through which the beam of charged particles for therapy passes caused by ionization of the tissue by the beam of charged particles for therapy.

17. The method of claim 9, wherein a pulse repetition frequency of the beam of charged particles for therapy is exactly equal to a resonance frequency of an MR signal generated by the MRI system from which the MRI data is acquired.

18. The method of claim 9, wherein using the MRI data to measure an actual trajectory of the beam of charged particles for therapy includes performing Blood Oxygen Level Dependent (BOLD) contrast functional imaging to detect a modulation of a resonance frequency in voxels through which the beam of charged particles for therapy passes which is produced by a root mean square (RMS) magnetic field around the beam of charged particles for therapy.

19. The method of claim 9, wherein using the MRI data to measure an actual trajectory of the beam of charged particles for therapy includes measuring a local decrease in T2 relaxation time of tissue through which the beam of charged particles for therapy passes caused by ionization of the tissue by the beam of charged particles for therapy.

20. The therapeutic apparatus of claim 1, wherein the MRI system includes an MRI magnet for generating the magnetic field, the therapeutic apparatus further comprising a shield for the guide, including an assembly of additional magnets distributed along the guide such that a component of the magnetic field in a plane through the path of the beam and an iso-center of the magnet, and perpendicular to the path of the beam, is cancelled by an additional magnetic field produced by the additional magnets.

* * * * *